US011383240B2

(12) United States Patent
Craighead et al.

(10) Patent No.: US 11,383,240 B2
(45) Date of Patent: Jul. 12, 2022

(54) SINGLE CELL WHOLE GENOME AMPLIFICATION VIA MICROPILLAR ARRAYS UNDER FLOW CONDITIONS

(71) Applicant: CORNELL UNIVERSITY, Ithaca, NY (US)

(72) Inventors: Harold G. Craighead, Ithaca, NY (US); Harvey C. Tian, Ithaca, NY (US)

(73) Assignee: CORNELL UNIVERSITY, Ithaca, NY (US)

(*) Notice: Subject to any disclaimer, the term of this patent is extended or adjusted under 35 U.S.C. 154(b) by 385 days.

(21) Appl. No.: 16/303,659

(22) PCT Filed: May 22, 2017

(86) PCT No.: PCT/US2017/033885
§ 371 (c)(1),
(2) Date: Nov. 20, 2018

(87) PCT Pub. No.: WO2017/205304
PCT Pub. Date: Nov. 30, 2017

(65) Prior Publication Data
US 2020/0316598 A1    Oct. 8, 2020

Related U.S. Application Data

(60) Provisional application No. 62/339,945, filed on May 22, 2016.

(51) Int. Cl.
*B01L 3/00* (2006.01)
*B01L 1/00* (2006.01)
*C12Q 1/6844* (2018.01)

(52) U.S. Cl.
CPC ... *B01L 3/502761* (2013.01); *B01L 3/502746* (2013.01); *C12Q 1/6844* (2013.01);
(Continued)

(58) Field of Classification Search
CPC ......... B01L 3/502761; B01L 3/502746; B01L 2300/0864
See application file for complete search history.

(56) References Cited

U.S. PATENT DOCUMENTS

| 5,304,487 A | 4/1994 | Wilding et al. |
| 6,696,022 B1 | 2/2004 | Chan et al. |

(Continued)

FOREIGN PATENT DOCUMENTS

| WO | 2007050040 A1 | 5/2007 |
| WO | 2011017677 A2 | 2/2011 |

(Continued)

OTHER PUBLICATIONS

Benitez et al., "Microfluidic Extraction, Stretching and Analysis of Human Chromosomal DNA from Single Cells," Lab Chip, 12(22):4848-4854 (Nov. 21, 2012).

(Continued)

*Primary Examiner* — Nathan A Bowers
(74) *Attorney, Agent, or Firm* — FisherBroyles, LLP; Andrew K. Gonsalves, Esq.

(57) ABSTRACT

The present invention relates to, inter alia, a microfluidic device for performing single cell genomic DNA isolation and amplification under flow. The microfluidic device comprises a solid substrate having one or more microfluidic channel system formed therein. Each microfluidic channel system of the microfluidic device comprises: (a) an intake region comprising a single microchannel; (b) a plurality of cell segregation microchannels; (c) a cell capture site located downstream of each cell segregation microchannel; and (d) a DNA capture array positioned downstream of the cell capture site and comprising a plurality of micropillars. Also disclosed is a whole genome amplification system that includes the microfluidic device of the present disclosure, as well as a method for conducting single cell DNA analysis via (Continued)

on-chip whole genome amplification while under flow, and a method for multiple displacement amplification (MDA) reactions of one or more nucleic acid sequence isolated single cells.

22 Claims, 10 Drawing Sheets

(52) U.S. Cl.
CPC .............. *B01L 2200/0647* (2013.01); *B01L 2300/0803* (2013.01); *B01L 2300/0864* (2013.01); *B01L 2400/0487* (2013.01); *B01L 2400/086* (2013.01)

(56) References Cited

U.S. PATENT DOCUMENTS

| | | |
|---|---|---|
| 7,964,978 B1 | 6/2011 | Lee et al. |
| 9,926,552 B2 | 3/2018 | Craighead et al. |
| 2002/0081744 A1 | 6/2002 | Chan et al. |
| 2002/0125192 A1 | 9/2002 | Lopez et al. |
| 2003/0143599 A1 | 7/2003 | Makarov et al. |
| 2003/0162181 A1 | 8/2003 | Yang et al. |
| 2004/0050700 A1 | 3/2004 | Lopez-Canovas et al. |
| 2004/0053403 A1 | 3/2004 | Jedrzejewski et al. |
| 2004/0142491 A1 | 7/2004 | Indermuhle et al. |
| 2005/0019819 A1 | 1/2005 | Tooke et al. |
| 2005/0064575 A1 | 3/2005 | Belgrader et al. |
| 2005/0069459 A1* | 3/2005 | Ahn .................. B01L 3/502753 422/504 |
| 2006/0133957 A1 | 6/2006 | Knapp et al. |
| 2007/0077547 A1 | 4/2007 | Shvets et al. |
| 2008/0124721 A1 | 5/2008 | Fuchs et al. |
| 2008/0125330 A1 | 5/2008 | Cady et al. |
| 2008/0274905 A1 | 11/2008 | Greene |
| 2009/0098541 A1* | 4/2009 | Southern .............. C12Q 1/6876 435/6.11 |
| 2009/0191563 A1 | 7/2009 | Steemers et al. |
| 2010/0047924 A1 | 2/2010 | Webster et al. |
| 2010/0137163 A1 | 6/2010 | Link et al. |
| 2011/0014605 A1 | 1/2011 | Stone |
| 2011/0027873 A1 | 2/2011 | Cho et al. |
| 2011/0212440 A1 | 9/2011 | Viovy et al. |
| 2014/0193812 A1 | 7/2014 | Hamilton et al. |
| 2014/0194313 A1 | 7/2014 | Craighead et al. |
| 2015/0018226 A1 | 1/2015 | Hansen et al. |
| 2016/0115470 A1* | 4/2016 | Cho ...................... C12M 35/02 435/34 |

FOREIGN PATENT DOCUMENTS

| | | |
|---|---|---|
| WO | 2011017681 A2 | 2/2011 |
| WO | 2011038241 A1 | 3/2011 |
| WO | 2014153071 A1 | 9/2014 |

OTHER PUBLICATIONS

International Searching Authority (WO/Isa), International Search Report and Written Opinion issued in PCT/US2017/033885, dated Aug. 16, 2017.

* cited by examiner

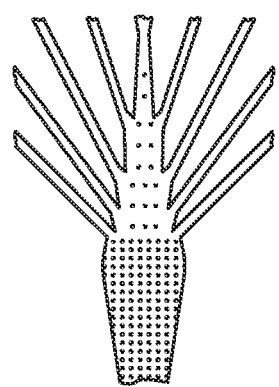 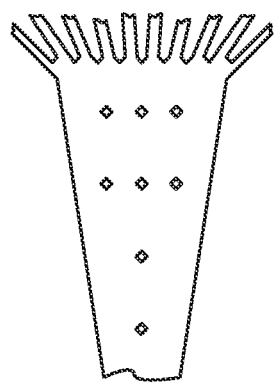
FIG.4D    FIG.4E
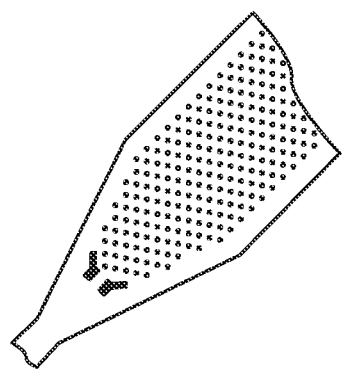 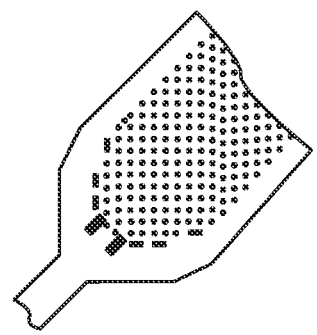 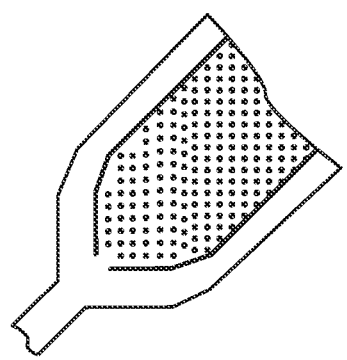
FIG.4F    FIG.4G    FIG.4H

SINGLE CELL WHOLE GENOME AMPLIFICATION VIA MICROPILLAR ARRAYS UNDER FLOW CONDITIONS

CROSS-REFERENCE TO RELATED APPLICATIONS

This application is a U.S. National Phase filing under 35 U.S.C. § 371 of International Application No. PCT/US2017/033885, filed May 22, 2017, and published as WO 2017/205304 A1 on Nov. 30, 2017, which claims priority benefit of U.S. Provisional Patent Application Ser. No. 62/339,945, filed May 22, 2016, the disclosures of which are hereby incorporated by reference herein in their entirety.

FIELD OF THE INVENTION

The present invention relates to, inter alia, microfluidic devices, systems, and methods for performing single cell genomic DNA isolation and amplification under flow conditions.

BACKGROUND OF THE INVENTION

Single cell analysis has become increasingly important for understanding and diagnosing disease [1-6]. For instance, cellular level aberrations have been shown to play critical roles in tumor heterogeneity, cancer metastasis, drug resistance, and cell fate [7-12]. Investigating these aberrations and differentiating between cell types within a population may give rise to improved treatments, however, single cell handling and analysis remains difficult. Due to having only picogram quantities of DNA, existing workflows cannot sequence single cell genomes directly without amplification due to sensitivity limits [13-15]. Thus, to obtain a sufficient quantity of material for sequencing, single cell WGA is necessary. Among most widely used single cell WGA amplification technique is multiple displacement amplification (MDA), which relies on a combination of random hexamer primers and the strand-displacement properties of the Phi29 polymerase to isothermally amplify DNA [14,15]. However, the primary technical challenge in using MDA for single cell WGA is random amplification bias resulting from chimera formation and non-linear enrichment [16-18]. This bias can be averaged out when analyzing monodisperse multi-cell population samples due to having a multiple copies of each gene. However, biases occurring on the single cell level lead to severe underrepresentation of genome regions that were not amplified early-on in the MDA reaction [19,31].

There is a need for new and improved technologies for isolating and amplifying DNA from a single cell without bias or with reduced bias. Such technologies are critical for ensuring that all or essentially all parts of a genome are more uniformly present in an amplified product. Such technology is important for enabling applications such as DNA sequencing and genetic analysis of a single cell or a few cells.

The present invention is directed to overcoming these and other deficiencies in the art.

SUMMARY OF THE INVENTION

The present invention provides, inter alia, microfluidic devices, systems, and methods for performing single cell genomic DNA isolation and amplification under flow conditions. In particular, as described herein, the present invention provides a microfluidic device that uses unique microfluidic channel systems having cell intake regions, cell segregation microchannels, cell capture sites, and DNA capture arrays containing micropillars for performing single cell genomic DNA isolation and amplification under flow conditions. As described herein, the present invention also provides a whole genome amplification system that includes the microfluidic device of the present disclosure. The present invention further provides a method for conducting single cell DNA analysis via on-chip whole genome amplification while under flow. Moreover, the present invention also provides a method for multiple displacement amplification (MDA) reactions of one or more nucleic acid sequence isolated single cells.

In one aspect, the present invention relates to a microfluidic device for performing single cell genomic DNA isolation and amplification under flow. The microfluidic device comprises a solid substrate having one or more microfluidic channel system formed therein. Each microfluidic channel system of the microfluidic device comprises: (a) an intake region comprising a single microchannel configured for receiving a plurality of cells and transporting them downstream to a cell capture staging region; (b) a plurality of cell segregation microchannels extending downstream from the cell capture staging region and configured for moving the cells further downstream; (c) a cell capture site located downstream of each cell segregation microchannel and comprising a structural barrier effective for physically capturing a single cell and arresting any further movement of the single cell through the microfluidic channel system; and (d) a DNA capture array positioned downstream of the cell capture site and comprising a plurality of micropillars configured and arranged in a manner effective for physically entangling and immobilizing thereon genomic DNA isolated from the captured single cell for use as DNA templates for one or more rounds of amplification of the isolated genomic DNA, said DNA capture array terminating in a collection region for collecting DNA amplification products of the isolated genomic DNA.

In one embodiment, the microfluidic device further comprises an input port comprising an opening extending into the solid substrate and being in fluidic connection to the intake region of the microfluidic channel system, said input port being configured for introducing cells into the microfluidic channel system.

In another embodiment, the microfluidic device further comprises an output reservoir comprising an opening extending out of the solid substrate and being in fluidic connection to the collection region of the DNA capture array, said output reservoir being configured for collecting DNA amplification products from the microfluidic channel system.

In yet another embodiment, the microfluidic device further comprises a bypass channel region comprising one or more bypass microchannel extending downstream from the cell capture staging region and connecting directly to the output reservoir, said bypass microchannel being configured to transport and expel non-arrested cells and other debris from the microfluidic device without passing through the DNA capture array.

In another embodiment, the DNA capture array of the microfluidic device further comprises a physical border comprising side walls surrounding the plurality of micropillars so as to prevent any non-captured cells from becoming lodged in the micropillars once a single cell is arrested at the cell capture site.

In another aspect, the present invention relates to a whole genome amplification system comprising: a microfluidic device according to the present disclosure, wherein said microfluidic device further comprises an input port and an output reservoir; and a pressure driven infusion apparatus for introducing fluids and cells into the microfluidic device. The pressure driven infusion apparatus comprises an infusion fluid chamber having a top end and a bottom end and a removable cap fitted to cover the top end of the infusion fluid chamber. The bottom end of the infusion fluid chamber is configured to connect to the input port of the microfluidic device so as to enable fluid to flow from the infusion fluid chamber into the input port. The removable cap is configured to connect to a gas source used for pressure driven flow of fluid from infusion fluid chamber into the input port and through the microfluidic channel system.

In another aspect, the present invention relates to a method for conducting single cell DNA analysis via on-chip whole genome amplification while under flow. This method comprises the steps of: providing a whole genome amplification system according to the present disclosure; introducing a plurality of cells into the microfluidic channel system using the pressure driven infusion apparatus; and operating the whole genome amplification system under conditions effective to capture a single cell in each of the cell capture cites of the cell segregation microchannels, physically entangle and immobilize genomic DNA from the single cell in the micropillars of the DNA capture array, and conduct one or more round of amplification of the isolated genomic DNA, thereby yielding DNA amplification products collected in the output reservoir of the whole genome amplification system.

In another aspect, the present invention relates to a method for multiple displacement amplification (MDA) reactions of one or more nucleic acid sequence isolated single cells. This method comprises the steps of: performing the steps of the method of the present disclosure for conducting single cell DNA analysis via on-chip whole genome amplification while under flow; and conducting multiple displacement amplification (MDA) reactions under flow using the genomic DNA entangled and maintained within the DNA entanglement array of the whole genome amplification system.

The microfluidic devices, whole genome amplification systems, and methods of using these devices and systems provide numerous advantages over existing technologies. For example, the present invention enables a method of performing multiple rounds of WGA (whole genome amplification) on the genomic DNA of a single cell. This is only possible by retaining the template DNA throughout the multiple rounds of WGA or else the template is lost as soon as one performs a first round of MDA. In certain applications, the microfluidic device of the present invention is designed to capture a single cell and arrest the genomic DNA of that cell once the cell has been lysed. The genomic DNA can then be retained within the microfluidic device of the present invention essentially indefinitely through multiple rounds of WGA.

Another advantage that the microfluidic device of the present invention provides is valveless, on-chip type of functionality for isolating and amplifying genomic DNA from single cells. Furthermore, in various embodiments, the microfluidic device of the present invention functions, in part, by physically entrapping genomic DNA from a cell after cell lysis, which is a mechanical approach that does not require specialized chemistry or affinity preparation of the micropillars or microchannels.

These and other objects, features, and advantages of this invention will become apparent from the following detailed description of the various aspects of the invention taken in conjunction with the accompanying drawings.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements.

FIG. 1A is a photograph of an embodiment of a microfluidic device of the present invention. FIG. 1B and FIG. 1C are illustrations of the top and side views, respectively, of the embodiment of the microfluidic device shown in the photograph of FIG. 1A. FIG. 1D are illustrations of the top view of the microfluidic device and of one of the four microfluidic channel systems contained in this embodiment of the microfluidic device of the present invention.

FIGS. 4A-4H illustrate aspects of a 10-channel device geometry and design of the microfluidic device of the present invention. FIG. 4A: Device schematic showing valveless 10-channel device design. FIG. 4B: Picture taken of 4 separate 10-channel devices made from a single PDMS slab bonded to a 4-inch diameter glass silica wafer. FIGS. 4C-4E: Chip design variations explored for the bifurcation point with FIG. 4E illustrating the final design used in various working examples described herein. FIGS. 4F-4H: Chip design variations explored for the individual channel cell capture region explored with FIG. 4H illustrating the final design used in various working examples described herein.

FIG. 5A: Flow moves from left to right in this schematic and fluids can be exchanged within the input reservoir to control the local environment within the channels. FIG. 5B: Artist depiction of a single cell that is trapped within the apex of the micropillar array. Side walls enclosing the micropillar array prevent additional cells flowing into the channel from having their DNA immobilized within the pillar array. FIG. 5C: Upon cell lysis, genomic DNA from the trapped cell will become entangled in downstream pillars and can be visualized via fluorescence staining. FIG. 5D: Reagents for whole genome amplification is flowed into the channel. As amplification occurs, product strands elongate originating from the template, but as they depart from the template genomic DNA, they are washed downstream and collected in output reservoirs.

FIG. 6A is a micrograph showing single cell capture. FIG. 6B illustrates subsequent lysed cell imaged under fluorescence with YOYO-1 intercalating dye staining of genomic DNA immobilized within the pillar array region.

DETAILED DESCRIPTION OF THE INVENTION

Figure 1A:
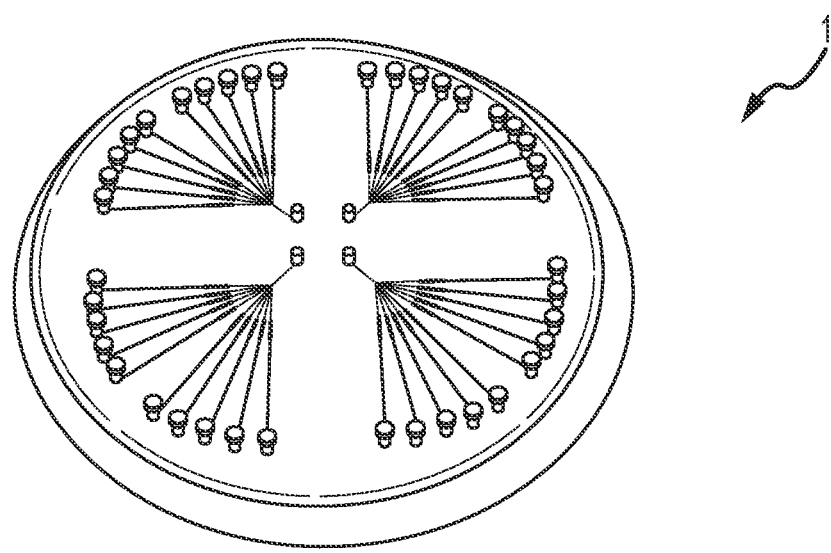
FIGS. 1A-1D illustrate various aspects of an embodiment of a microfluidic device of the present invention.

The present invention relates to, inter alia, microfluidic devices, systems, and methods for performing single cell genomic DNA isolation and amplification under flow conditions.

More particularly, the present invention provides a microfluidic device that uses unique microfluidic channel systems having cell intake regions, cell segregation microchannels, cell capture sites, and DNA capture arrays containing micropillars for performing single cell genomic DNA isolation and amplification under flow conditions. As described herein, the present invention also provides a whole genome amplification system that includes the microfluidic device of the present disclosure. The present invention further provides a method for conducting single cell DNA analysis via on-chip whole genome amplification while under flow. Moreover, the present invention also provides a method for multiple displacement amplification (MDA) reactions of one or more nucleic acid sequence isolated single cells.

In one aspect, the present invention relates to a microfluidic device for performing single cell genomic DNA isolation and amplification under flow. The microfluidic device comprises a solid substrate having one or more microfluidic channel system formed therein. Each microfluidic channel system of the microfluidic device comprises: (a) an intake region comprising a single microchannel configured for receiving a plurality of cells and transporting them downstream to a cell capture staging region; (b) a plurality of cell segregation microchannels extending downstream from the cell capture staging region and configured for moving the cells further downstream; (c) a cell capture site located downstream of each cell segregation microchannel and comprising a structural barrier effective for physically capturing a single cell and arresting any further movement of the single cell through the microfluidic channel system; and (d) a DNA capture array positioned downstream of the cell capture site and comprising a plurality of micropillars configured and arranged in a manner effective for physically entangling and immobilizing thereon genomic DNA isolated from the captured single cell for use as DNA templates for one or more rounds of amplification of the isolated genomic DNA, said DNA capture array terminating in a collection region for collecting DNA amplification products of the isolated genomic DNA.

In one embodiment, the microfluidic device further comprises an input port comprising an opening extending into the solid substrate and being in fluidic connection to the intake region of the microfluidic channel system, said input port being configured for introducing cells into the microfluidic channel system.

In another embodiment, the microfluidic device further comprises an output reservoir comprising an opening extending out of the solid substrate and being in fluidic connection to the collection region of the DNA capture array, said output reservoir being configured for collecting DNA amplification products from the microfluidic channel system.

In yet another embodiment, the microfluidic device further comprises a bypass channel region comprising one or more bypass microchannel extending downstream from the cell capture staging region and connecting directly to the output reservoir, said bypass microchannel being configured to transport and expel non-arrested cells and other debris from the microfluidic device without passing through the DNA capture array.

In certain embodiments, the bypass channel region comprises a first bypass microchannel running alongside a first side of the DNA capture array and a second bypass microchannel running alongside a second and opposite side of the DNA capture array.

In another embodiment, the DNA capture array of the microfluidic device further comprises a physical border comprising side walls surrounding the plurality of micropillars so as to prevent any non-captured cells from becoming lodged in the micropillars once a single cell is arrested at the cell capture site.

The number of microfluidic channel systems formed in solid substrate can vary depending on the desired use. In certain embodiments, the solid substrate can include, without limitation, 1 or more separate microfluidic channel systems formed therein. In certain embodiments, the solid substrate can include, without limitation, more than 5, 10, 15, 20, 25, 30, 35, 40, 45, 50, 60, 70, 80, 90, 100, 200, 300, 400, or 500 separate microfluidic channel systems formed therein. The present invention contemplates the use of any number of microfluidic channel systems covered by these ranges. In a more particular embodiment, the solid substrate includes between 1 and 10 separate microfluidic channel systems formed therein.

The number of cell segregation microchannels extending downstream from each cell capture staging region of the microfluidic microfluidic channel system can vary depending on the desired use. In certain embodiments, each microfluidic channel system can include, without limitation, 2 or more cell segregation microchannels extending downstream from each cell capture staging region. In certain other embodiments, each microfluidic channel system can include, without limitation, at least 3, at least 4, at least 5, at least 6, at least 7, at least 8, at least 9, at least 10, at least 15, at least 20, at least 25, at least 30, at least 35, at least 40, at least 45, at least 50, at least 60, at least 70, at least 80, at least 90, at least 100 cell segregation microchannels extending downstream from each cell capture staging region. The present invention contemplates the use of any number of cell segregation microchannels covered by these ranges.

In certain embodiments, the single microchannel of the intake region can have dimensions that include, without limitation, a width of between about 10 µm and about 2500 µm, a height of between about 0.1 µm and about 1000 and a length of between about 50 µm and about 30 cm. The present invention contemplates the use of any dimensions for the microchannels covered by these ranges.

In certain other embodiments, the single microchannel of the intake region can have dimensions that include, without limitation, a width of between about 50 µm and about 250 µm, a height of between about 8 µm and about 20 µm, and a length of between about 1 cm and about 5 cm. The present invention contemplates the use of any dimensions for the microchannels covered by these ranges.

In certain embodiments, the micropillars can have, without limitation, a diameter ranging from between about 0.5 µm and about 15 The present invention contemplates the use of any dimensions for the micropillars covered by these ranges.

In certain embodiments, the micropillars can have, without limitation, a diameter ranging from between about 1.5 µm and about 2 µm.

The micropillars can be arranged in various configurations. In certain embodiments, the micropillars can be arranged in a gradient so that the spacing between the micropillars narrows in a downstream manner. In a more particular embodiment, the gradient of micropillars comprises 1-3 distinct regions located downstream of one another, each distinct region having its own uniform spacing of micropillars.

The solid substrate of the microfluidic device of the present disclosure can be made from various materials, including, without limitation, such materials as polydimethylsiloxane (PDMS), polystyrene, epoxy, polymethylmethacrylate (PMMA), silica, and such other glass, metal, and plastic materials.

In one embodiment, the solid substrate can be made of a material such as PDMS and then mounted onto another supportive structure (also referred to herein as a bottom layer connected to the bottom of the solid substrate), such as one made of fused silica, as shown herein. In one embodiment, the microfluidic device can be made using standard soft-lithography and/or mold-replica techniques. In another embodiment, the microfluidic device can be made using standard direct lithography and/or injection molding.

The micropillars of the microfluidic device of the present disclosure can be made from various materials, including, without limitation, a material selected from the group consisting of polydimethylsiloxane (PDMS), glass, and plastics.

With respect to the micropillars, although they are used to entangle and immobilize genomic DNA, they also can be configured to provide other functions. For example, certain of the micropillars can be used to provide structural integrity to the microfluidic channel system so as to prevent structural collapse during negative pressure.

The microfluidic device of the present invention can be used to incorporate various technologies relating to microfluidic arrays, microfluidic cell capture, nucleic acid elongation and capture, and the like. Such compatible technologies described in the art can be found in various published U.S. patent applications, including, without limitation, the following (which are incorporated herein by reference in their entirety): US-2015/0291952, US-2015/0204859, US-2014/0121132, US-2014/0194313, and US-2015/0011425. For example, in various non-limiting embodiments, the DNA capture arrays of the present invention and the micropillars contained therein can be designed, arranged, and fabricated as taught in US-2014/0194313, which is incorporated herein by reference in its entirety.

In another aspect, the present invention relates to a whole genome amplification system comprising: a microfluidic device according to the present disclosure, wherein said microfluidic device further comprises an input port and an output reservoir; and a pressure driven infusion apparatus for introducing fluids and cells into the microfluidic device. The pressure driven infusion apparatus comprises an infusion fluid chamber having a top end and a bottom end and a removable cap fitted to cover the top end of the infusion fluid chamber. The bottom end of the infusion fluid chamber is configured to connect to the input port of the microfluidic device so as to enable fluid to flow from the infusion fluid chamber into the input port. The removable cap is configured to connect to a gas source used for pressure driven flow of fluid from infusion fluid chamber into the input port and through the microfluidic channel system.

In another aspect, the present invention relates to a method for conducting single cell DNA analysis via on-chip whole genome amplification while under flow. This method comprises the steps of: providing a whole genome amplification system according to the present disclosure; introducing a plurality of cells into the microfluidic channel system using the pressure driven infusion apparatus; and operating the whole genome amplification system under conditions effective to capture a single cell in each of the cell capture cites of the cell segregation microchannels, physically entangle and immobilize genomic DNA from the single cell in the micropillars of the DNA capture array, and conduct one or more round of amplification of the isolated genomic DNA, thereby yielding DNA amplification products collected in the output reservoir of the whole genome amplification system.

In a particular embodiment of this method, the step of operating the whole genome amplification system comprises applying flow pressure through the microfluidic channel system at a flow rate effective to perform the following sub-steps in sequence: (i) a first sub-step of transporting the plurality of cells from the intake region to the cell capture staging region; (ii) a second sub-step of segregating single cells into the cell segregation microchannels; (iii) a third sub-step of physically capturing a single cell at the cell capture site of each cell segregation microchannel; (iv) a fourth sub-step of releasing genomic DNA from the captured single cells into each corresponding DNA capture array, thereby causing the released genomic DNA to become physically entangled and immobilized on the micropillars; and (v) a fifth sub-step of amplifying the immobilized genomic DNA under flow for one or more rounds so as to yield DNA amplification products from the immobilized genomic DNA.

In accordance with this method, the flow rate can be adjusted as desired by the operator. In one embodiment of this method, the flow rate can range from between about 0 µL/minute and about 50 µL/minute, without limitation. The present invention contemplates the use of any of the flow rates (IL/minute) covered by this range.

The method can be used to isolate and amplify, under flow, genomic DNA from single cells, single cell nuclei, single cell fragments, or any other structure containing genomic DNA or portions of genomic DNA. As used herein, to identify the source of genomic DNA, the term "cell" is meant to be a catch-all term that covers all of these sources of genomic DNA. By way of example, the plurality of cells can comprise, without limitation, cancer cells and any other type of cell for which the study of genomic DNA is desired.

In another aspect, the present invention relates to a method for multiple displacement amplification (MDA) reactions of one or more nucleic acid sequence isolated single cells. This method comprises the steps of: performing the steps of the method of the present disclosure for conducting single cell DNA analysis via on-chip whole genome amplification while under flow; and conducting multiple displacement amplification (MDA) reactions under flow using the genomic DNA entangled and maintained within the DNA entanglement array of the whole genome amplification system.

FIGS. 1-7 provide schematic, photographic, and photomicrographic views of illustrative embodiments and aspects of the microfluidic device of the present invention, as well as the systems (e.g., whole genome amplification system) that include the microfluidic device of the present invention. While the aforementioned figures relate to and are further described in the examples provided herein below, certain of these figures are helpful in describing the microfluidic device and related systems in general terms.

Figure 1B:
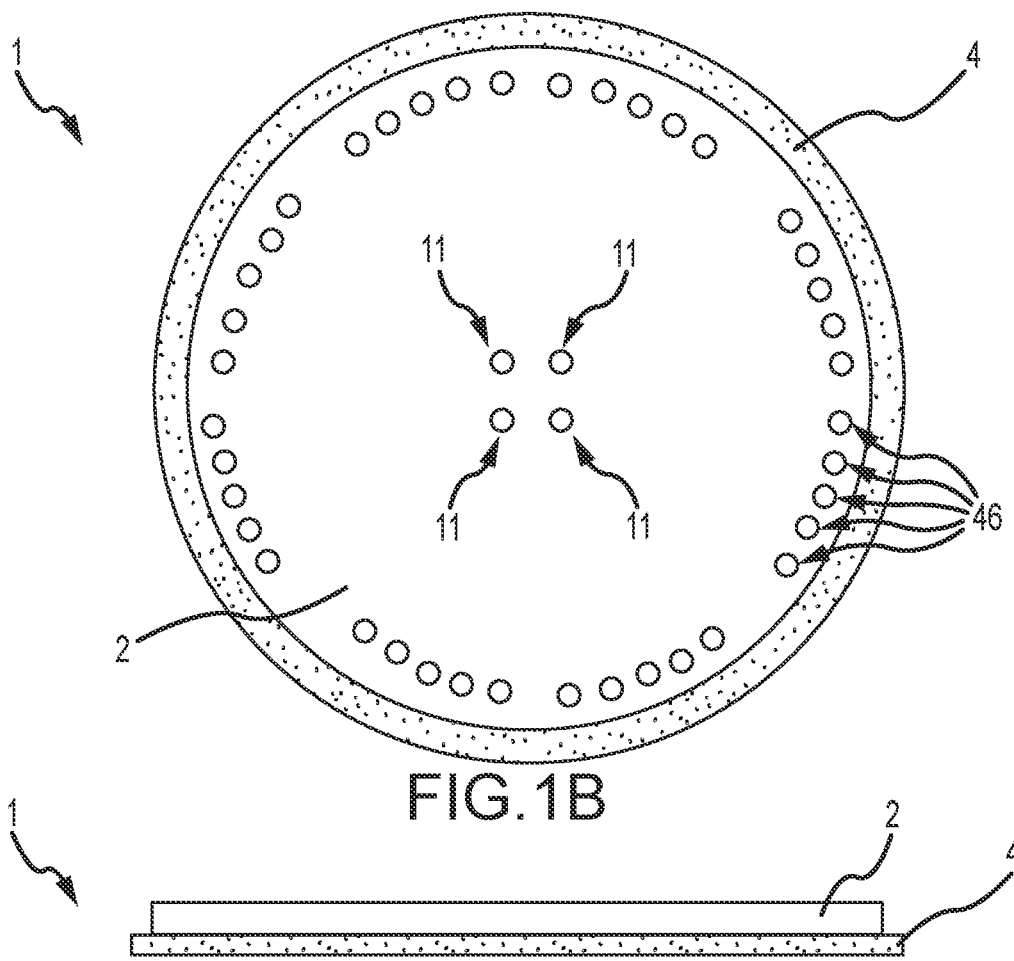
Figure 1C:
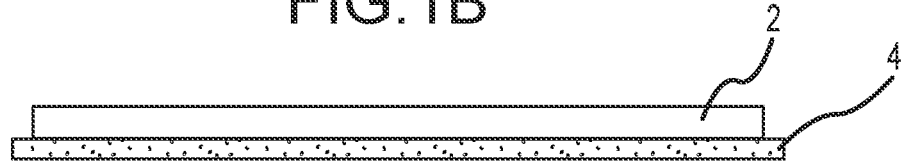
Figure 1D:
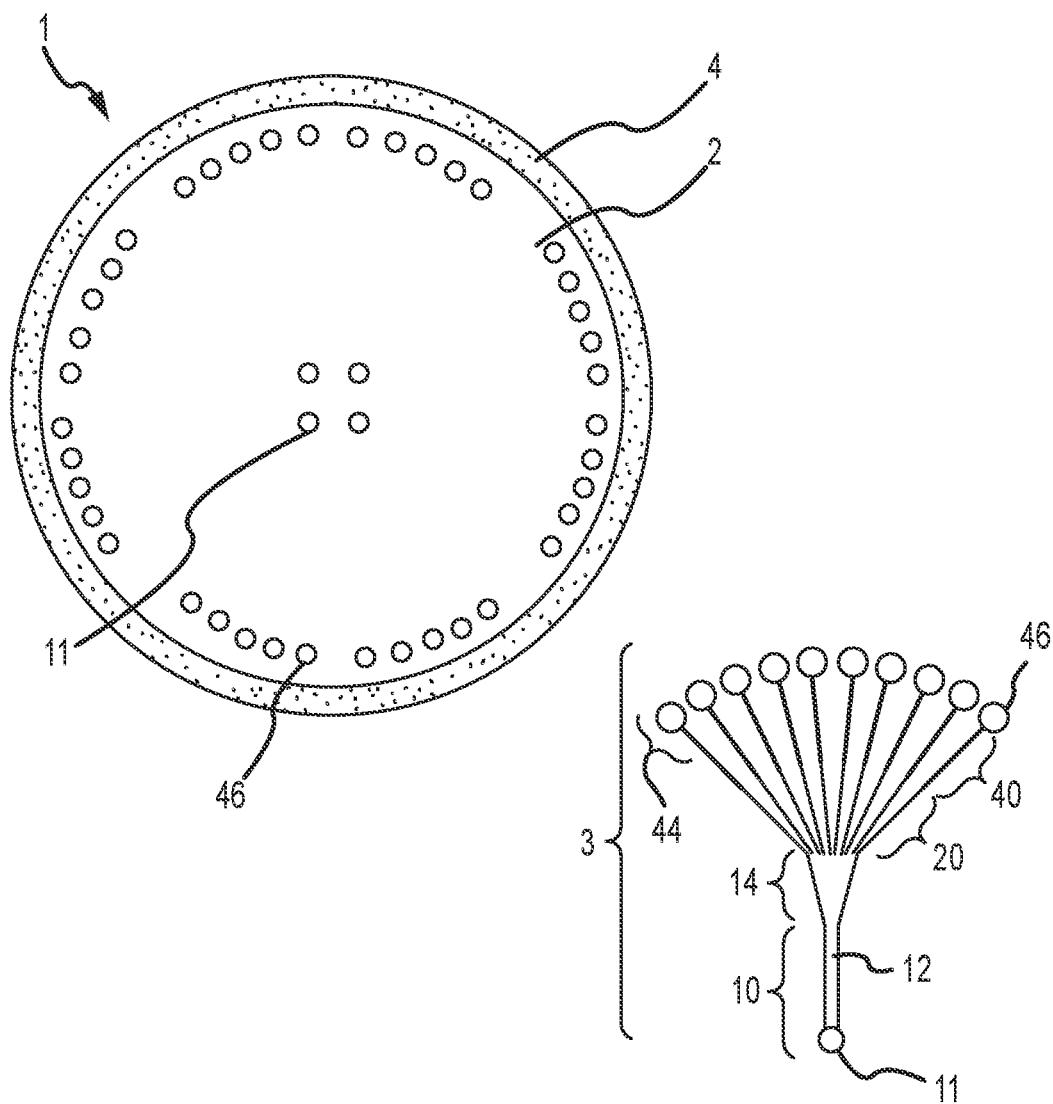

FIGS. 1A-1D illustrate various aspects of an embodiment of microfluidic device 1 of the present invention. In particular, FIG. 1A is a photograph of an embodiment of microfluidic device 1 of the present invention. Further description of how to make and use microfluidic device of FIG. 1A is set forth in the Examples section hereof. FIG. 1B is an illustration of the top view microfluidic device 1, while FIG. 1C is an illustration of a side view of microfluidic device 1. FIG. 1D are illustrations of the top view of microfluidic device 1 and of one of the four microfluidic channel systems 3 contained in this embodiment of microfluidic device 1 of the present invention.

As shown in FIG. 1B, microfluidic device 1 includes solid substrate 2 having bottom layer 4 (e.g., a glass silica wafer) bonded thereto (e.g., via oxygen-plasma bonding). As shown in FIG. 1B, solid substrate 2 includes four input ports 11 and a plurality of output reservoirs 46 (80 input ports are shown in FIG. 1B). The embodiment of microfluidic device 1 of FIG. 1B is configured so that one quadrant contains one microfluidic channel system, although the present invention is not limited to this configuration. In the particular configuration of FIG. 1B, each quadrant includes one input port 11 that is in microfluidic connection with ten output reservoirs 46, so that the flow of liquid enters input port 11 and exits through output reservoirs 46. Input ports 11 and output reservoirs 46 are the starting and terminating ends of the microfluidic channel system portion of microfluidic device 1. FIG. 1B, which is just a top view of microfluidic device 1, does not show the rest of the microfluidic channel system, although in practice the microfluidic channel system could be visible if solid substrate 2 is made of a transparent or semi-transparent material (e.g., PDMS). FIG. 1C is a side view of microfluidic device 1 and shows solid substrate 2 mounted on bottom layer 4.

Figure 2:
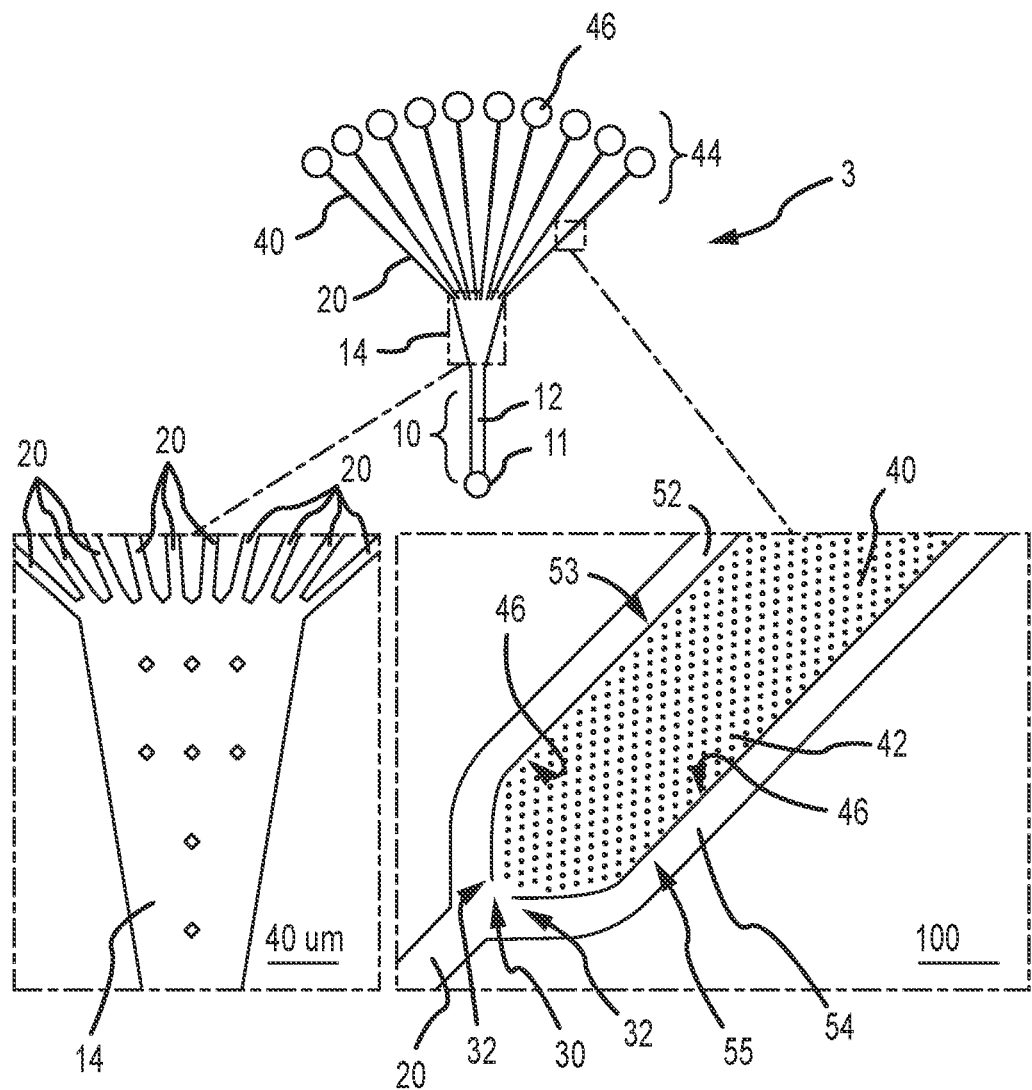
FIG. 2 is a schematic illustration of various aspects of an embodiment of the microfluidic channel system of the microfluidic device of the present invention.

Turning to FIG. 1D, there is shown the top view of microfluidic device 1 and of one of the four microfluidic channel systems 3 contained in this embodiment of microfluidic device 1 of the present invention. FIG. 2 provides a more detailed view of various aspects of microfluidic channel system 3 of microfluidic device 1. As shown in FIG. 1D and FIG. 2, each microfluidic channel system 3 of microfluidic device 1 includes the following: (a) intake region 10 comprising a single microchannel 12 configured for receiving a plurality of cells and transporting them downstream to a cell capture staging region 14; (b) a plurality of cell segregation microchannels 20 extending downstream from the cell capture staging region 14 and configured for moving the cells further downstream; (c) a cell capture site 30 located downstream of each cell segregation microchannel 20 and comprising a structural barrier 32 effective for physically capturing a single cell and arresting any further movement of the single cell through microfluidic channel system 3; and (d) a DNA capture array 40 positioned downstream of cell capture site 30 and comprising a plurality of micropillars 42 configured and arranged in a manner effective for physically entangling and immobilizing thereon genomic DNA isolated from the captured single cell for use as DNA templates for one or more rounds of amplification of the isolated genomic DNA. The DNA capture array 40 terminates in a collection region 44 for collecting DNA amplification products of the isolated genomic DNA. As shown in FIG. 1D and FIG. 2, test samples and buffers are introduced through input port 11 of intake region 10 and exit through output reservoirs 46.

Turning to FIG. 2, in various embodiments, microfluidic device 1 can further include a bypass channel region comprising one or more bypass microchannel (52, 54) extending downstream from cell capture staging region 14 and connecting directly to output reservoir 46. As shown in FIG. 2, in certain embodiments, the bypass microchannel can be configured to transport and expel non-arrested cells and other debris from microfluidic device 1 without passing through DNA capture array 40. As shown in FIG. 2, in certain embodiments, the bypass channel region comprises a first bypass microchannel 52 running alongside a first side 53 of DNA capture array 40 and a second bypass microchannel 54 running alongside a second and opposite side 55 of DNA capture array 40. Also as shown in FIG. 2, in various embodiments, DNA capture array 40 of microfluidic device 1 can further include a physical border comprising side walls 46 surrounding the plurality of micropillars 42 so as to prevent any non-captured cells from becoming lodged in micropillars 42 once a single cell is arrested at cell capture site 30.

Figure 3:
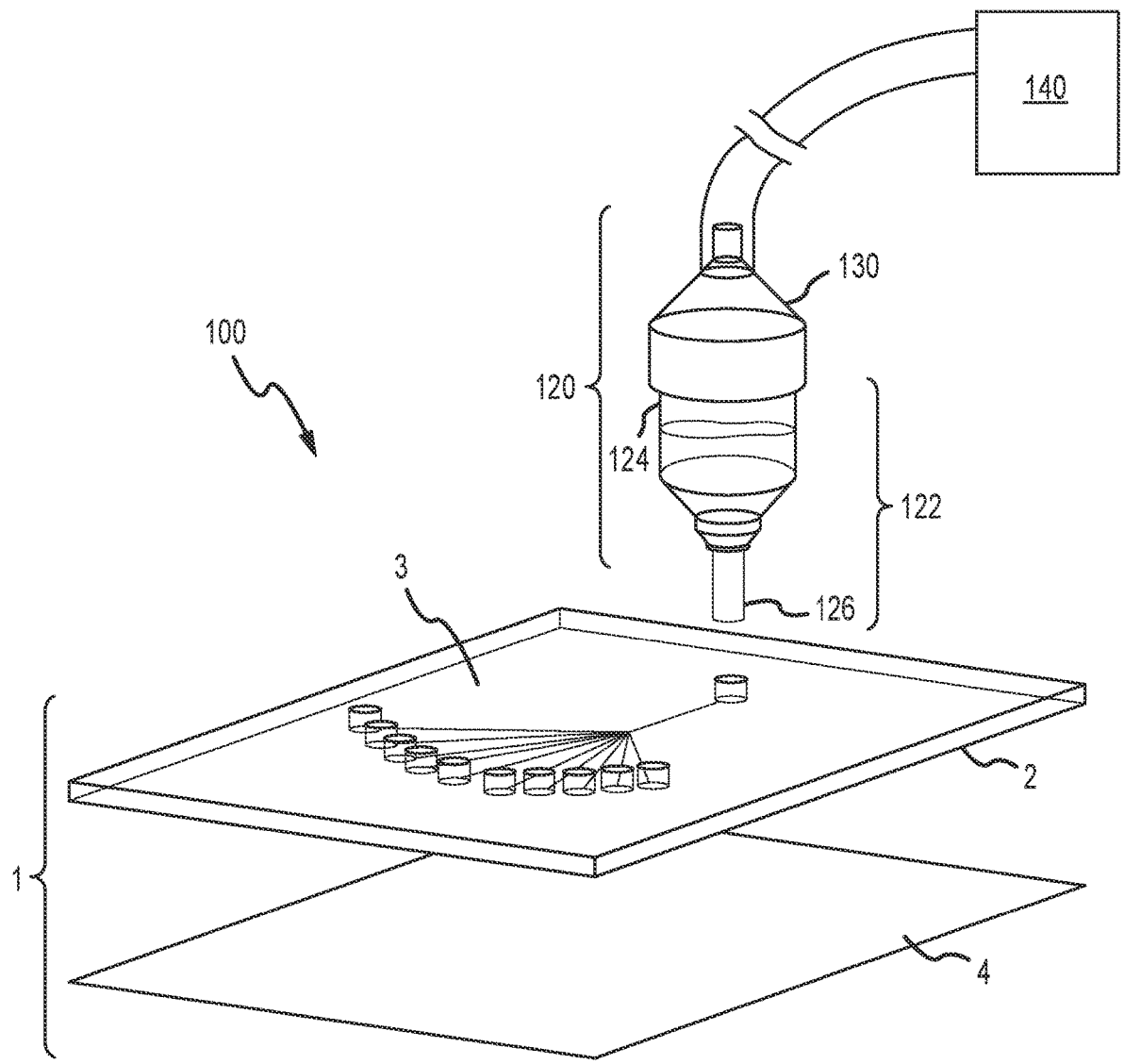
FIG. 3 is a schematic illustration of one embodiment of a whole genome amplification system of the present invention.

FIG. 3 is a schematic illustration of one embodiment of a whole genome amplification system of the present invention. As shown in FIG. 3, whole genome amplification system 100 of the present invention includes the following: a microfluidic device 1 according to the present disclosure and pressure driven infusion apparatus 120. Pressure driven infusion apparatus 120 assists in introducing fluids and cells into microfluidic device 1. As shown in FIG. 3, pressure driven infusion apparatus 120 includes an infusion fluid chamber 122 having a top end 124 and a bottom end 126 and a removable cap 130 fitted to cover the top end 124 of the infusion fluid chamber 122. The bottom end 126 of infusion fluid chamber 122 is configured to connect to the input port of microfluidic device 1 so as to enable fluid to flow from the infusion fluid chamber 122 into the input port. Removable cap 130 is configured to connect to a gas source 140 used for pressure driven flow of fluid from infusion fluid chamber 122 into the input port and through the microfluidic channel system.

This embodiment of the whole genome amplification system 100 shown in FIG. 3 is of a GAMA experimental setup overview. Mold-casted PDMS (solid substrate 2) containing a single input port and 10 parallel output ports are bonded to glass silica (bottom layer 4) via oxygen-plasma bonding. An infusion apparatus (pressure driven infusion apparatus 120) is connected to the input port to provide pressure driven flow of desired fluids. Liquid can be manually loaded into the infusion apparatus at will.

EXAMPLES

The following examples are intended to illustrate particular embodiments of the present invention, but are by no means intended to limit the scope of the present invention.

Example 1

Single Cell Whole Genome Amplification Via Micropillar Arrays

Single cell whole genome amplification (WGA) has long suffered from amplification biases that reduce the accuracy of single cell sequencing data. To this end, an easily adoptable process requiring minimal microfabrication complexity remains desirable. Here, we describe genomic amplification via micropillar array (GAMA) on single human cancer cells from the HeLa cell line. This micropillar array is designed to capture single cells and physically entangle its chromosomal DNA in a fixed position throughout WGA. By testing for the presence of 6 gene loci along the human genome, we demonstrate an improved genome coverage and reduced amplification bias using GAMA as opposed to conventional fluorescence activated cell-sorting (FACS) based single cell assays.

To this end, several techniques have been found to minimize amplification bias during MDA by reducing reaction volumes [20]. Although the mechanism by which reducing amplification volume reduces bias remains to be fully explained, it has been demonstrated across a number of platforms. These platforms can be broadly categorized into limiting dilution technologies [21], droplet microfluidic technologies [22-24], and chambered microfluidic technologies [25]. Limiting dilution technologies provide a high degree of parallelism, but the microwells can suffer from cross-contamination of liquids and reagents [21]. More reliable compartmentalization of single cell genomic material can be achieved via emulsion enclosure and microfluidic chambers, however complex channel geometries and valving systems are required to achieve an integrated platform capable of both single cell isolation and genomic analysis. Hence, exploring alternative methodologies of integrating cell capture and genomic analysis is a critical component of the overall effort to improve single cell sequencing.

Recently, our group has developed a valveless microfluidic device for on-chip single cell capture and DNA extraction [26]. The core of this technology uses micropillar arrays to physically entrap genomic DNA (gDNA) from cells upon lysis. As this process is purely mechanical, it does not require any chemical modification or cell sample preparation.

Here, we utilized the unique advantages conferred by micropillar arrays as a basis for developing GAMA, a novel microfluidics-based approach towards single cell WGA. GAMA relies on the high capture efficiency and DNA immobilization properties of micropillar arrays to hold template gDNA in a fixed position within the microchannel as reagents for WGA are flowed through. This approach differs fundamentally from previously mentioned technologies in that the template gDNA is subjected to a constant flow throughout the amplification process while the amplified product is washed downstream and collected in the output reservoir. To demonstrate the viability of our approach, we use GAMA to perform MDA-based WGA of single cells and compare the genome coverage, determined by the successful amplification of select gene loci, to conventional assays based on fluorescence activated cell sorting (FACS).

Materials and Methods

Cell Culture:

HeLa-GFP cells were cultured in Dulbecco's Modified Eagle medium (DMEM) (Invitrogen) within a T75 flask at 37 C and 5% CO2. Cell culture medium was supplemented with 10% fetal bovine serum (FBS) (Atlanta Biologicals; Atlanta, Ga.), 1% (wt) non-essential amino acids (NEAA) (Gibco, Life Technologies), 1% (wt) L-glutamine (Gibco, Life Technologies), 2% (wt) HEPES (Quality Biological; Gaithersburg, Md.), and 0.1% of 1:100 dilution 2-mercaptoethanol (βME) (Sigma-Aldrich; St. Louis, Mo.). Cells were passaged at 60% (vl) confluency roughly twice per week.

General Photolithography for Microfluidic Device Fabrication:

General photolithography fabrication steps for making microfluidic devices can include, without limitation, the following workflow. Silicon molds for polydimethylsiloxane (PDMS) microfluidic devices can be fabricated using standard photolithography techniques. Briefly, wafers (Ultrasil; Hayward, Calif.) are spin coated with Microposit S1813 photoresist (Shipley; Marlborough, Mass.). Device pattern is transferred onto photoresist layer using UV contact lithography (ABM contact aligner, ABM-USA; San Jose, Calif.). Exposed substrates are developed in 726MIF developer (Microchemicals). The microfluidic pattern can be transferred onto the top silicon layer by Bosch process in a Unaxis SLR 770 deep reactive ion etching system (Unaxis USA Inc.; St. Petersburg, Fla.). Etch depth was determined to be 20-25 μm using a P10 profilometer (KLA Tencor; Milipitas, Calif.) and a Zygo otical profilometer (Zygo Corporation; Middlefield, Conn.). A monolayer of (1H,1H, 2H,2H-Perfluorooctyl) Trichlorosilane can be deposited on the etched wafers in a MVD100 molecular wafer deposition system (Applied Microstructures; San Jose, Calif.) to prevent adhesion of PDMS to the mold.

Sylgard 184 (Dow Corning; Midland, Mich.) PDMS base resin can be mixed with the curing agent at a 10:1 ratio, degassed under vacuum at room temperature, poured onto the master until a 1 cm thick layer was achieved, and then heat cured for 45 minutes at 150 C. The elastomer casting can then be peeled off the mold and access holes to the input and outputs of the microchannels were created via 1.5 mm biopsy punch (Sklar Instruments; West Chester, Pa.). To complete channel fabrication, the patterned PDMS can be treated with oxygen plasma for 5 minute and bonded to a 500 μm thick fused silica wafer (Mark Optics; Santa Ana, Calif.).

A further example of a process for microfluidic device photolithography is outlined as follows: Starting with a clean 4-inch diameter silicon wafer surface, photoresist is spin coated onto the surface. The pattern is then exposed and developed before the photoresist is stripped and the wafer is the wafer is etched. To prevent polymer binding on the surface during mold-casting, a thin layer of FOTS is vapor deposited onto the silicon master. To fabricate the polymer microfluidic device, PDMS base mixed with curing agent is poured onto the silicon master. After removing the cured silicon slab containing the pattern, it is then plasma bonded onto a glass silica wafer to create the final microfluidic device.

Device Fabrication:

General photolithography fabrication steps were done in accordance with the methods outlined in the preceding section. However, PDMS was mixed at a ratio of 12:1 base resin to curing agent, rather than 10:1, and was heat cured at a lower temperature 100 C for one hour in a Sheldon oven. Also, the design of the single cell microfluidic channels mask was vastly different than that of the original microfluidic pillar array based cell processor. Rather than having a single input port lead to a single output port, we increased the throughput of the device by splitting the output into 10 separate but identical channels.

Single Cell Capture and Lysis:

HeLa-GFP cells were trypsinized from T75 flasks with 0.25% Trypsin. Trypsinized cells neutralized with 1:1 dilution of phosphate buffered saline (PBS) buffer, spun down in a centrifuge, and then resuspended in fresh PBS at a concentration of 1:50. The cell suspension was flowed into the microfluidic device via pressure driven flow at 2 psi with bone-dry nitrogen gas (Airgas; Radnor Township, Pa.). The infusion apparatus was then disconnected from the microfluidic device's input port, washed with alternating cycles of 100% ultrapure water (Invitrogen; Carlsbad, Calif.) and 100% ethanol to remove the remaining cells within the reservoir, and then reconnected to the microfluidic device input port. Sterile PBS buffer was then flowed into the microfluidic device for 5 minutes to allow uncaptured cells to either be captured within the cell capture region or to flow through the device into the output reservoirs. The output reservoirs of the device were then emptied and rinsed with 100% ultrapure water.

Lysis buffer comprised of 6M guanidinium thiocyanate (Sigma-Aldrich; St. Louis, Mo.) in water was flowed into the microfluidic device for 5 minutes also by pressure driven flow at 2 psi. After visually confirming cell lysis in all ten channels, the lysis buffer was removed from the input reservoir and the reservoir rinsed with 100% ethanol before flushing the entire microfluidic device with 100% ethanol for 5 minutes. The ethanol is replaced by washing with 100% ultrapure water for 5 minutes and then finally replaced by PBS buffer. The output reservoirs that now contain a mixture of cell lysates, lysis buffer, ethanol, water, and PBS was then emptied and cleaned via rinsing first with 100% ethanol and then 100% ultrapure water. The genomic DNA tethered within the microfluidic device is now ready for whole genome amplification.

On-Chip Whole Genome Amplification:

Whole genome amplification (WGA) of the single cell genomic DNA tethered within the micropillar array region of the microfluidic device was carried out using reagents from the REPLI-g UltraFast Mini Kit (Qiagen; Hilden, Germany). Prior to starting the reaction, 280 ul of buffer D1 was made by adding 35 ul of buffer DLB to 245 ul of ultrapure H2O. 400 ul of buffer Ni was then prepared by adding 40 ul of stop solution to 360 ul of ultrapure H2O. Finally, 288 ul of master mix was made by adding 18 ul of polymerase to 270 ul Repli-G UltraFast reaction buffer.

To denature the double stranded gDNA tethered on the micropillar array, buffer D1 was flowed through the device continuously at room temperature for 8 minutes. Buffer D1 was then removed and the device was flushed with buffer N1 for 15 minutes. Afterwards, both the infusion apparatus and the ten output reservoirs were emptied and washed with 100% ethanol and then 100% ultrapure water. The infusion apparatus was then loaded with the master mix solution and pressure was dialed down to 0.5 psi. Pressure was then held constant throughout the entire duration of the 3.5 hour reaction amplification reaction while the device was placed atop a hot-plate set to 33 C. After the reaction was completed, 5 ul of ultrapure H2O was added to each output reservoir. Each output reservoir was then pipette mixed and the solution containing amplified genomic DNA was collected off-chip into a polymerase chain reaction (PCR) tube. Each output reservoir was then rinsed once more with 10 ul of ultrapure H2O and the rinse was collected into the respective PCR tube containing the amplified product. All samples were placed in a −20 C freezer until further use.

FACS Single Cell WGA:

A FACS machine (Becton Dickinson Biosciences; San Jose, Calif.) was used to sort single HeLa-GFP cells into a PCR-compatible microwell plate (Bio-Rad; Hercules, Calif.) with each well containing 5 ul of sterile PBS buffer. The microwell plate was then spun down in centrifuge at 1000 g for 5 minutes to ensure that sorted single cells were sitting at the bottom of their respective wells. Buffer D2 and master mix were then prepared according to the Repli-g UltraFast kit's protocol. To lyse the single cells in each microwell, 5 ul of buffer D2 was added to each well and incubated on ice for 10 minutes. 5 ul of stop solution was then added to each well and incubated on ice for 5 minutes. Finally, 53.3 ul of master mix was added to each well and the microwell plate was placed in a thermocycler (Eppendorf; Germany) set to hold at 30 C for 3.5 hours.

Gene Loci PCR:

Primers were designed to target 150 bp-200 bp regions within six gene loci (ERBB2 17q12, PRMT2 21q22, P53 17p13, CCND1 11q13, TRAM1 8q13, and MyC8q24) and ordered through Integrated DNA Technologies (IDT; Coralville, Iowa). Lyophilized primers were dissolved in water to a concentration of 10 μM. Then, following the protocols from the Taq DNA Polymerase Kit (Life Technologies; Carlsbad, Calif.), 50 ul reaction were prepared for each of the 6 gene loci for every collected single cell WGA sample. 30 cycles of PCR were carried out and the PCR product was run on a 2.3% agarose gel via electrophoresis. Using a 2-log ladder (New England Biosciences; Ipswich, Mass.), the appropriate size region of 100 bp-200 bp was evaluated for the presence or absence of the gene.

Results

Channel Design and Experimental Setup:

FIG. 3 shows the overall experimental setup for GAMA. To create the chip device, a slab of mold-casted PDMS (polydimethylsiloxane) imprinted with the channel geometry is bonded to a glass slide to create the microfluidic device. Reagents are loaded into the device via pressure driven flow from an infusion apparatus housing a large fluid reservoir. Fluid that is loaded into the infusion reservoir can be easily exchanged and replaced via pipetting. The infusion apparatus is a two-part mechanism consisting of a reservoir portion that can be connected to the PDMS and a cap that is connected to the nitrogen gas cylinder used to drive channel flow.

Figure 4A:
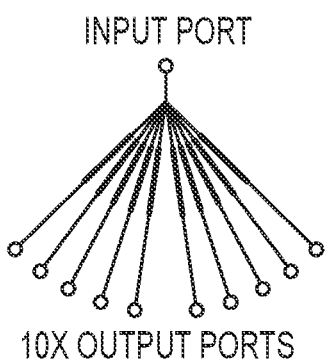
Figure 4B:
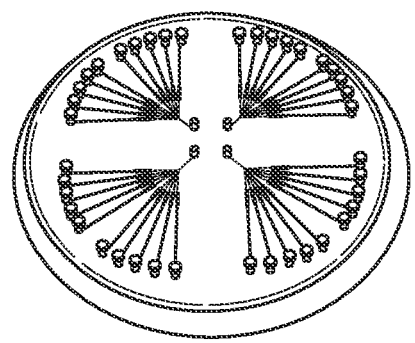
Figure 4C:
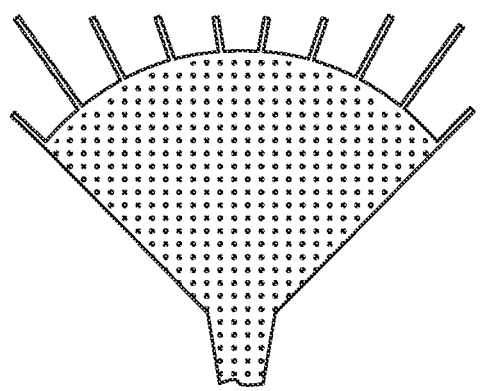
Figure 5A:
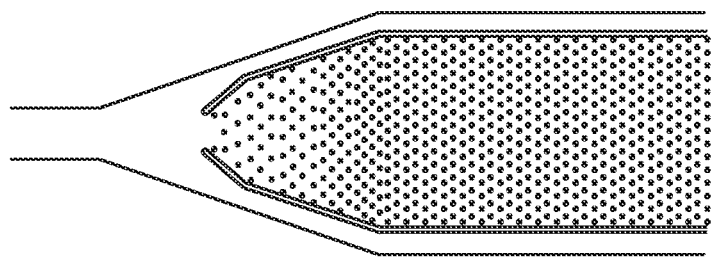
FIGS. 5A-5D are schematics illustrating aspects of a GAMA process workflow involving the use of a microfluidic channel system of the present invention.
Figure 5B:
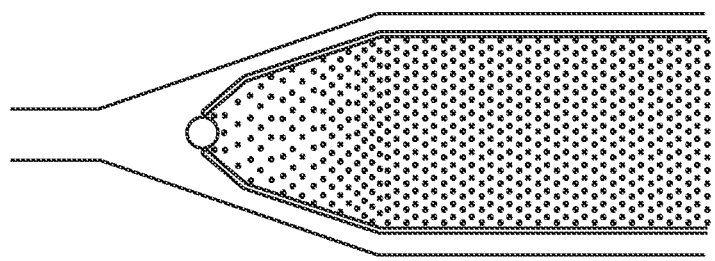
Figure 5C:
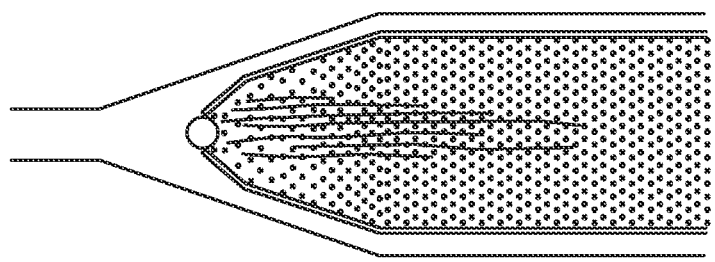
Figure 5D:
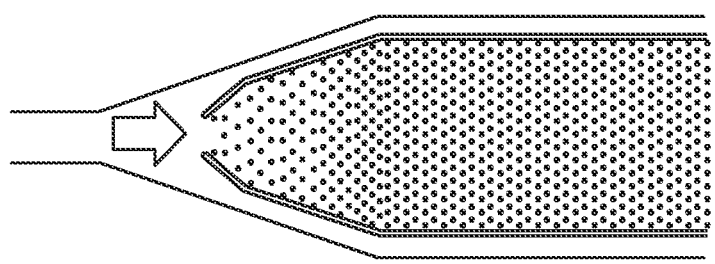
Figure 5D:
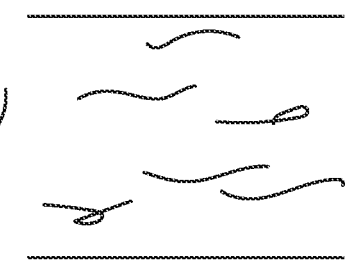

FIGS. 4A-4H show a top down view of the device design. The GAMA device has a single input port and 10 separate output ports allowing multiple single cell samples to be run in parallel. These ten channels each contain identical designs consisting of a single cell capture region and micropillar array (FIG. 4A). To show the device in scale, FIG. 4B shows four such devices can be casted from a 4-inch silicon wafer mold as a single slab and bonded to a glass-silica wafer. Experiments were run with the microfluidic device mounted on the stage of an Olympus IX-70 inverted microscope (Olympus; Center Valley, Pa.) to image and observe the microfluidic channels in real time.

Figure 6A:
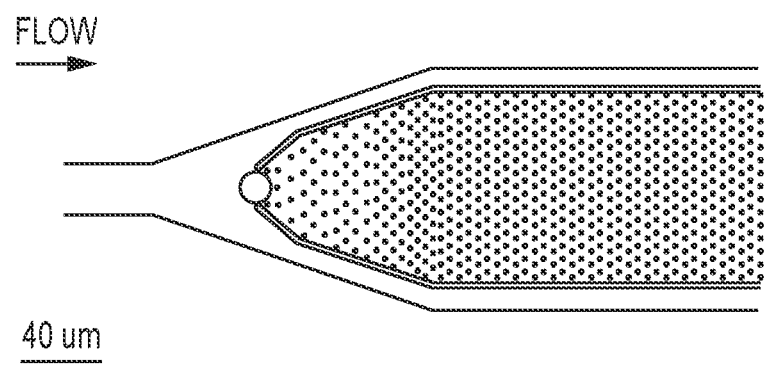
FIGS. 6A-6B illustrate single cell capture and DNA extraction.
Figure 6B:
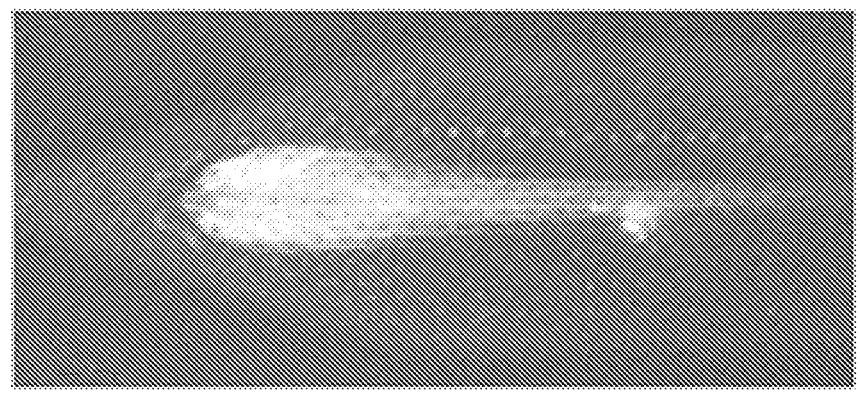

Single Cell Whole Genome Amplification On-Chip:

As depicted by the graphic in FIG. 6A, the single cell capture region consists of a series of posts arranged in an orientation to allow only a single cell to be arrested in the apex of the micropillar array. Barriers surrounding the micropillar array prevent non-arrested cells from lodging themselves in the micropillar array. Upon introduction of lysis buffer, the micropillar array will physically immobilize the gDNA. This immobilization process occurs as a result of the chromosomal DNA being physically entangled on the pillars due to their centimeter scale lengths, while smaller cellular debris such as lipids, proteins, RNA, and mDNA (mitochondrial DNA) are washed away downstream. The immobilized gDNA can be imaged via fluorescent staining with DNA intercalating dye labels such as with YOYO-1 in FIG. 6B.

To perform single cell GAMA on the immobilized gDNA tethered within the microfluidic chip, we used MDA with reagents from the commercially available Repli-G UltraFast Mini Kit (Qiagen). An illustration of the GAMA workflow can be seen in FIGS. 5A-5D. After cell capture and lysis, FIG. 5B, denaturation buffer D1 was prepared according to Repli-G kit protocols and flowed into the microfluidic device to cleave the hydrogen bonds of the double stranded gDNA into single stranded DNA. Buffer D1 was then neutralized by flushing the channel with neutralization buffer N1. Finally, the master mix containing bases and polymerase was introduced to the channels and the microfluidic chip was set atop a heated hot plate to initiate the amplification reaction. Although we had initial concerns that denatured DNA molecules would rapidly reanneal during the amplification step due to being suspended in close proximity to complimentary strands, we saw no evidence of this reannealing behavior occurring.

Another concern was that the highly branched structures characteristic of isothermal amplification with Phi29 would occlude our channels, however we did not observe any buildup or clogging of the device. We reason that this is because the average sized fragments produced from the MDA, roughly 12 kb in length, are too small to wrap around the 1.5 µm diameter PDMS micropillars without slipping off. Furthermore, the amplification reaction occurs under a constant flow, thus, as soon as the amplified fragment is detached from its template strand, it is carried downstream along established flow lines into the corresponding output reservoir.

The amplified DNA can then be collected from the output reservoirs and the gDNA tethered within the micropillar array can be washed and amplified again in further rounds. The advantage conferred from multiple rounds of amplification using GAMA is that regions of the genome that are randomly overrepresented in one amplification will not carry into the next amplification. This is because random amplification bias occurs as a result of the exponential growth in the number of fragments in the reaction as the reaction progresses. Thus, regions of the genome that are amplified first will quickly pull ahead in representation over regions of the genome that are not amplified until later in the reaction. With GAMA, the amplified product can be collected while the template gDNA is still retained within the channels thereby "resetting" the molecule count of the next amplification round. Averaged over multiple amplification rounds, GAMA would theoretically remove random amplification bias and improve genome coverage. As random amplification bias is inherent in single cell MDA, GAMA is a necessary process to obtain full genome coverage.

Validation and Gene Loci Detection:

For the reason that MDA has been shown to produce non-specific product in a prolonged reaction, simply quantifying the amount DNA collected from the output reservoirs is insufficient to determine the success or failure of the on-chip single cell GAMA process. To differentiate DNA amplified from gDNA versus non-specific product, 6 different gene loci in the human genome were selected to act as sampling intervals. Using the product collected from GAMA as a template for PCR, the presence or absence of each of the 6 gene loci was evaluated as a means of assessing the bias and overall genome coverage of GAMA.

Figure 7:
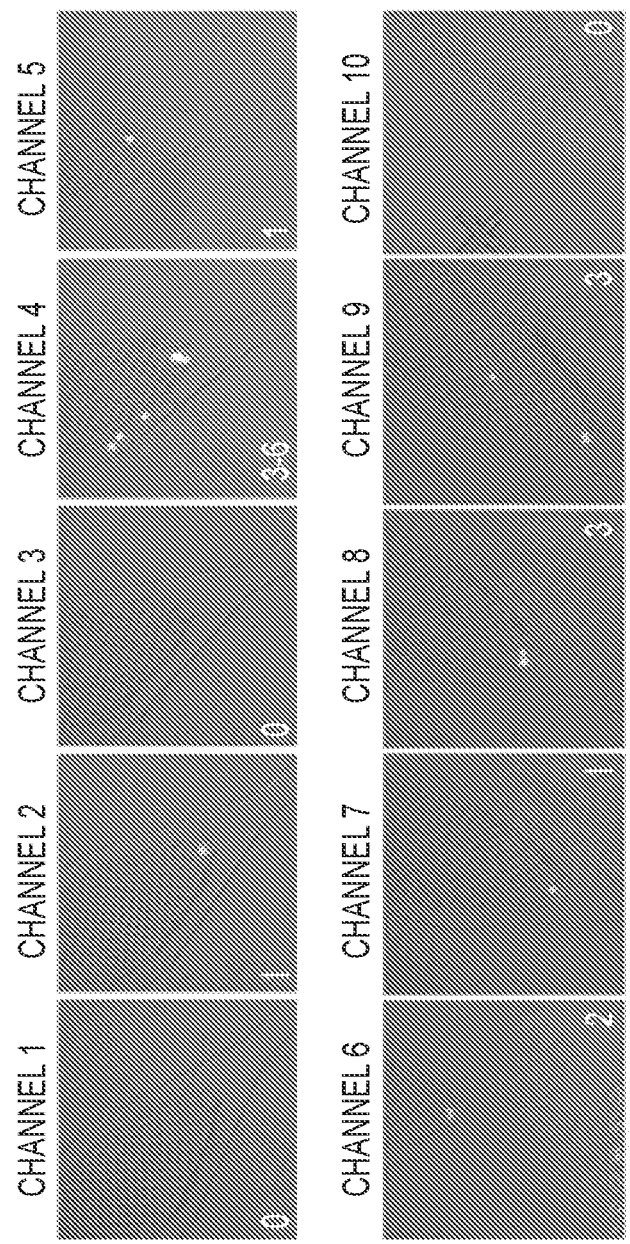
FIG. 7 are micrographs illustrating HeLa-GFP cell capture in a 10-channel device. Compiled series of micrographs taken from the cell capture region of a single 10-channel device. Channels containing single cells (2, 5, & 7) are analyzed in comparison to empty channels (1, 3, & 10), which serve as negative controls from the same device.
Figure 8:
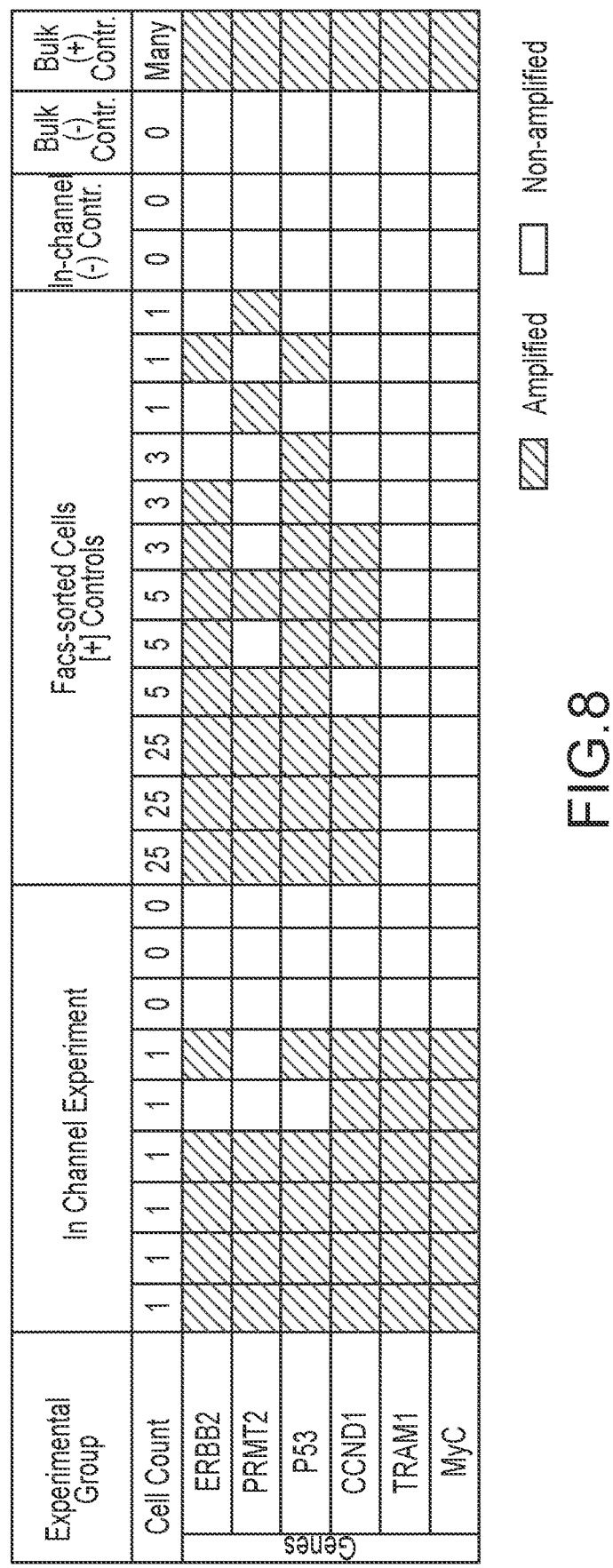
FIG. 8 is a table illustrating gene loci detection of in-channel versus FACS single cell WGA compared with positive and negative controls. Compiled table of genome coverage analyzed by detection of 6 cancer-relevant gene loci. Using GAMA, single cell WGA reflects up to 6/6 gene loci detected versus up to 2/6 gene loci detected using conventional single cell WGA via FACS. In-channel single cell negative controls with 0 cells expectedly show no gene loci coverage and off-chip bulk-level analysis affirms the specificity of primers used in loci detection.

FIG. 8 shows the number of gene loci detected from six single cells amplified with GAMA as well as the number of gene loci detected from bulk (107 cells) using the same Repli-G UltraFast kit. On-chip negative controls with 0 cells expectedly did not amplify any gene loci. Furthermore, as the two main sources of potential contamination that may occur are (1) unaccounted cells trapped being within the microfluidic channel and (2) off-chip sample handling, we ran an experiment where a single device had channels containing both a single cell as well as a negative no-cell control. FIG. 7 shows micrographs taken from the cell capture region of the 10 channels in a single device. Channels containing a single HeLa-GFP cell (2, 5, and 7) were compared to channels with 0 cells (1, 3, and 10) in the number of gene loci detected post GAMA. While it was found that many of the gene loci were present in the GAMA product collected from single cell channels, 0 gene loci were detected in empty channels on the same device. This result eliminates the possibility of on-chip contamination being a contributing factor in gene loci detection. Samples from channels such as channel 4, 6, 8, and 9 are disregarded due to having multiple cells. Factors contributing to the capture of multiple cells within a channel are that the channel dimensions and micropillar spacing need to be further optimized for the specific cell type being used and rarely, cells become adhered onto the glass surface within the device due to non-specific binding. In future iterations of the device, non-specific cell adherence can be prevented though treating the glass surface with blocking agents or charge-shielding the channel.

Single Cell WGA with FACS:

To compare our on-chip single cell GAMA results to single cell WGA in absence of a micropillar array, we performed Fluorescence Activated Cell Sorting (FACS) to isolate various numbers of cells into PCR-compatible 96-well plates and amplified the gDNA from these cells using the same reaction times and reagents. Our findings, shown in FIG. 8, is that when maintaining the same WGA parameters as GAMA, FACS isolated single cells only amplified one or two gene loci compared to the 4 to 6 amplified by the GAMA process. Finally, past work has observed MDA to exhibit random bias behaviors on the single cell level but non-random bias on a multi-cell level [13,27-30]. Our FACS results support this claim as we have observed that biases occurring in samples of 25 cells consistently underrepresent the same gene loci whereas single cell bias showed no such pattern.

CONCLUSION

We have described a micropillar-based microfluidic device capable of on-chip single cell processing and WGA. Unlike conventional single cell platforms, GAMA is capable of physically separating the template gDNA from the amplified product during WGA as well as controlling the fluid environment surrounding the gDNA. This property allows GAMA to be used in overcoming random amplification bias such as when performing single cell WGA with MDA. Here, we have demonstrated a reduced amplification bias for single cell WGA using GAMA. This was accomplished by showing that we could reliably amplify more gene loci of the genome from single HeLa cells using GAMA as opposed to single cells isolated through FACS. It is envisioned that one would be able to use GAMA for multiple rounds of amplification performed in series on a single genome template. Doing so would reset the product pool molecule count at each intermediate washing step, thereby resetting the amplification bias for each round. Subsequently, compiling the randomly over-represented regions of each amplification round may serve as a means to improve total genome coverage in bias-vulnerable amplification scenarios such as single cell WGA.

REFERENCES

Citation of a reference herein shall not be construed as an admission that such reference is prior art to the present invention. All references cited herein are hereby incorporated by reference in their entirety. Below is a listing of various references cited herein by Reference ("Ref.) number:
1. K. R. Chi, Nature Methods, 2014, 11, 13-17
2. E. Shapiro, T. Biezuner, S. Linnarsson, Nature Reviews Genetics, 2013, 14, 618-630
3. X. Zhang, S. L. Marjani, Z. Hu, S. M. Weissman, X. Pan, S. Wu, Cancer Research, 2016, 76(6), 1305-1312
4. N. E. Navin, J. Hicks, Genome Medicine, 2011, 3(31), 1-12
5. K. Galler, K. Brautigam, C. Grobe, J. Popp, U. Neugebauer, Analyst, 2014, 139, 1237-1273
6. C. E. Sims, N. L. Allbritton, Lab Chip, 2007, 7, 423-440
7. X. Liu, F. Long, H. Peng, S. J. Aerni, M. Jiang, A. Sanchez-Blanco, J. I. Murray, B. Mericle, S. Batzoglou, E. W. Myers, S. K. Kim, Cell, 2009, 139(3), 623-633
8. G. Guo, M. Huss, G. Q. Tong, C. Wang, L. L. Sun, N. D. Clarke, P. Robson, Developmental Cell, 2010, 18(4), 675-685
9. P. Dalerba, T. Kalisky, D. Sahoo, P. S. Rajendran, M. E. Rothenberg, A. A. Leyrat, S. Sim, J. Okamoto, D. M. Johnston, D. Qian, M. Zabala, J. Bueno, N. F. Neff, J. Wang, A. A. Shelton, B. Visser, S. Hisamori, Y. Shimono, M. Wetering, H. Clevers, M. F. Clarke, S. R. Quake, 2011, 29(12), 1120-1130
10. Powell, A. H. Talasaz, H. Zhang, M. A. Coram, A. Reddy, G. Deng, M. L. Telli, R. H. Advani, R. W. Carlson, J. A. Mollick, S. Sheth, A. W. Kurian, J. M. Ford, F. E. Stockdale, S. R. Quake, R. F. Pease, M. N. Mindrinos, G. Bhanot, S. H. Dairkee, R. W. Davis, S. S. Jeffrey, PloS One, 2012, 7(5), e33788
11. G. Deng, S. Krishnakumar, A. A. Powell, H. Zhang, M. N. Mindrinos, M. L. Telli, R. W. Davis, S. S. Jeffrey, BMC Cancer, 2014, 14:456
12. L. Paguirigan, J. Smith, S. Meshinchi, M. Carroll, C. Maley, J. P. Radich, Science Translational Medicine, 2015, 7(281), pp. 281re2
13. C. F. de Bourcy, I. D. Vlaminck, J. N. Kanbar, J. Wang, C. Gawad, S. R. Quake, PloS One, 2014, 9(8), e105585
14. N. E. Navin, Genome Biology, 2014, 15:452
15. R. S. Lasken, Biochem Soc Trans, 2009, 37(2), 450-453
16. R. S. Lasken, T. B. Stockwell, BMC Biotech, 2007, 7:19
17. S. Rodrigue, R. R. Malmstrom, A. M. Berlin, B. W. Birren, M. R. Henn, S. W. Chisholm, PloS One, 2009, 4(9), e6864
18. M. Chen, P. Song, D. Zou, X. Hu, S. Zhao, S. Gao, F. Ling, Plos One, 2014, 9(12), e114520
19. Y. Yang, H. S. Rho, M. Stevens, A. G. Tibbe, H. Gardeniers, L. W. Terstappen, Lab Chip, 2015, 15, 4331-4337
20. C. A. Hutchison, H. O. Smith, C. Pfannkoch, J. C. Venter, PNAS, 2005, 102(48), 17332-17336
21. J. Gole, A. Gore, A. Richards, Y. J. Chiu, H. L. Fung, D. Bushman, H. I. Chiang, J. Chun, Y. H. Lo, K. Zhang, Nature Biotech, 2013, 31(12), 1126-1134
22. M. Sidore, F. Lan, S. W. Lim, A. R. Abate, Nucleic Acids Research, 2015, 1-9
23. Y. Fu, C. Li, S. Lu, W. Zhou, F. Tang, X. S. Xie, Y. Huang, PNAS, 2015, 12(38), 11923-11928
24. Y. Nishikawa, M. Hosokawa, T. Maruyama, K. Yamagishi, T. Mori, H. Takeyama, Plos One, 2015, 10(9), e0138733
25. Y. Marcy, T. Ishoey, R. S. Lasken, T. B. Stockwell, B. P. Walenz, A. L. Halpern, K. Y. Beeson, S. M. Goldberg, S. R. Quake, Plos Genetics, 2007, 3(9), 1702-1708
26. J. J. Benitez, J. Topolancik, H. C. Tian, C. B. Wallin, D. R. Latulippe, K. Szeto, P. J. Murphy, B. R. Cipriany, S. L. Levy, P. D. Soloway, H. G. Craighead, Lab Chip, 2012, 12, 4848-4854
27. C. Z. Zhang, V. A. Adalsteinsson, J. Francis, H. Cornils, J. Jung, C. Maire, K. L. Ligon, M. Meyerson, J. C. Love, Nature Communications, 2015, 6 (6822), 1-10
28. Y. Fu, C. Li, S. Lu, W. Zhou, F. Tang, X. S. Xie, Y. Huang, PNAS, 2015, 112(38), 11923-11928
29. Raghunathan, H. R. Ferguson, C. J. Bornarth, W. Song, M. Driscoll, R. S. Lasken, App Environmental Microbiology, 2005, 71(6), 3342-3347
30. K. Zhang, A. C. Martiny, N. B. Reppas, K. W. Barry, J. Malek, S. W. Chrisholm, G. M. Church, Nature Biotech, 2006, 24(6), 680-686
31. K. M. Ellegaard, L. Klasson, S. G. Andersson, PloS One, 2013, 8(11), e82319

Although the present invention has been described for the purpose of illustration, it is understood that such detail is solely for that purpose and variations can be made by those skilled in the art without departing from the spirit and scope of the invention which is defined by the following claims.

What is claimed is:

1. A whole genome amplification system comprising a microfluidic device, said microfluidic device comprising:
(i) a solid substrate having one or more microfluidic channel system formed therein, wherein each microfluidic channel system comprises:
(a) an intake region comprising a single microchannel configured for receiving a plurality of cells and transporting them downstream to a cell capture staging region;
(b) a plurality of cell segregation microchannels extending downstream from the cell capture staging region and configured for moving the cells further downstream;
(c) a cell capture site located downstream of each cell segregation microchannel and comprising a structural barrier effective for physically capturing a single cell and arresting any further movement of the single cell through the microfluidic channel system; and
(d) a DNA capture array positioned downstream of the cell capture site and comprising a plurality of micropillars configured and arranged in a manner effective for physically entangling and immobilizing thereon genomic DNA isolated from the captured single cell for use as DNA templates for one or more rounds of amplification of the isolated genomic DNA, said DNA capture array terminating in a collection region for collecting DNA amplification products of the isolated genomic DNA;
(ii) an input port and an output reservoir; and
(iii) a pressure driven infusion apparatus for introducing fluids and cells into the microfluidic device, wherein said pressure driven infusion apparatus comprises an infusion fluid chamber having a top end and a bottom end and a removable cap fitted to cover the top end of the infusion fluid chamber, wherein said bottom end of the infusion fluid chamber is configured to connect to the input port of the microfluidic device so as to enable fluid to flow from the infusion fluid chamber into the input port, and wherein said removable cap is configured to connect to a gas source used for pressure driven flow of fluid from infusion fluid chamber into the input port and through the microfluidic channel system.

2. The whole genome amplification system according to claim 1, wherein said input port comprises an opening extending into the solid substrate and being in fluidic connection to the intake region of the microfluidic channel system, said input port being configured for introducing cells into the microfluidic channel system.

3. The whole genome amplification system according to claim 1, wherein said output reservoir comprises an opening extending out of the solid substrate and being in fluidic connection to the collection region of the DNA capture array, said output reservoir being configured for collecting DNA amplification products from the microfluidic channel system.

4. The whole genome amplification system according to claim 3 further comprising:

a bypass channel region comprising one or more bypass microchannel extending downstream from the cell capture staging region and connecting directly to the output reservoir, said bypass microchannel being configured to transport and expel non-arrested cells and other debris from the microfluidic device without passing through the DNA capture array.

5. The whole genome amplification system according to claim 4, wherein the bypass channel region comprises a first bypass microchannel running alongside a first side of the DNA capture array and a second bypass microchannel running alongside a second and opposite side of the DNA capture array.

6. The whole genome amplification system according to claim 1, wherein the DNA capture array further comprises a physical border comprising side walls surrounding the plurality of micropillars so as to prevent any non-captured cells from becoming lodged in the micropillars once a single cell is arrested at the cell capture site.

7. The whole genome amplification system according to claim 1, wherein the solid substrate comprises between 1 and 10 separate microfluidic channel systems formed therein.

8. The whole genome amplification system according to claim 1, wherein each microfluidic channel system includes 2 or more cell segregation microchannels extending downstream from each cell capture staging region.

9. The whole genome amplification system according to claim 1, wherein the single microchannel of the intake region has a width of between about 10 μm and about 2500 μm, a height of between about 0.1 μm and about 1000 μm, and a length of between about 50 μm and about 30 cm.

10. The whole genome amplification system according to claim 1, wherein the single microchannel of the intake region has a width of between about 50 μm and about 250 μm, a height of between about 8 μm and about 20 μm, and a length of between about 1 cm and about 5 cm.

11. The whole genome amplification system according to claim 1, wherein the micropillars have a diameter ranging from between about 0.5 μm and about 15 μm.

12. The whole genome amplification system according to claim 1, wherein the micropillars have a diameter ranging from between about 1.5 μm and about 2 μm.

13. The whole genome amplification system according to claim 1, wherein the micropillars are arranged in a gradient so that the spacing between the micropillars narrows in a downstream manner.

14. The whole genome amplification system according to claim 13, wherein said gradient of micropillars comprises 1-3 distinct regions located downstream of one another, each distinct region having its own uniform spacing of micropillars.

15. The whole genome amplification system according to claim 1, wherein the solid substrate is made from a material selected from the group consisting of polydimethylsiloxane (PDMS), glass, metals, and plastics.

16. The whole genome amplification system according to claim 1, wherein the micropillars are made from a material selected from the group consisting of polydimethylsiloxane (PDMS), glass, and plastics.

17. The whole genome amplification system according to claim 1, wherein each cell segregation microchannel extends downstream to a channel wider than the cell segregation microchannel comprising the micropillar array and the structural barrier enclosed by side walls of the wider channel and the structural barrier and an apex of the micropillar array forms the cell capture site located inside the channel.

18. The whole genome amplification system according to claim 1, wherein the structural barrier extends downstream to form a physical border and wherein the physical border is arranged to:

(i) surround the micropillar array configured to prevent non-arrested cells from lodging in the micropillar array;

(ii) form a first side wall of a first bypass microchannel running alongside a first side of the micropillar array; and (iii) form a second side wall of a second bypass microchannel running alongside a second and opposite side of the micropillar array.

19. The whole genome amplification system according to claim 1, further comprising a plurality of output reservoirs, wherein each output reservoir is positioned downstream of the DNA capture array such that a sample loaded in the input port can be run in parallel and the fluid in each of the plurality of output reservoirs is capable of being collected by a pipette such that a plurality of single cells are capable of being analyzed in parallel.

20. The whole genome amplification system according to claim 1, wherein the cell capture staging region comprises a plurality of micropillars.

21. The whole genome amplification system according to claim 1, wherein at least 3 cell segregation microchannels are directly extending from each cell capture staging region.

22. A method for conducting single cell DNA analysis via on-chip whole genome amplification while under flow, said method comprising the steps of:

providing a whole genome amplification system according to claim 1;

introducing a plurality of cells into the microfluidic channel system using the pressure driven infusion apparatus; and operating the whole genome amplification system under conditions effective to capture a single cell in each of the cell capture cites of the cell segregation microchannels, physically entangle and immobilize genomic DNA from the single cell in the micropillars of the DNA capture array, and conduct one or more round of amplification of the isolated genomic DNA, thereby yielding DNA amplification products collected in the output reservoir of the whole genome amplification system.

* * * * *